US00PP29688P2

(12) United States Plant Patent
Geibel

(10) Patent No.: US PP29,688 P2
(45) Date of Patent: Sep. 18, 2018

(54) ***PELARGONIUM* PLANT NAMED 'PACCHOGI'**

(50) Latin Name: *Pelargonium x hortorum*
Varietal Denomination: Pacchogi

(71) Applicant: Martin Geibel, Dresden (DE)

(72) Inventor: Martin Geibel, Dresden (DE)

(73) Assignee: Elsner pac Jungpflanzen GbR, Dresden (DE)

( * ) Notice: Subject to any disclaimer, the term of this patent is extended or adjusted under 35 U.S.C. 154(b) by 0 days.

(21) Appl. No.: 15/530,941

(22) Filed: Mar. 28, 2017

(51) Int. Cl.
*A01H 5/02* (2018.01)

(52) U.S. Cl.
USPC ..... Plt./330

(58) Field of Classification Search
USPC ..... Plt./324, 325, 330
See application file for complete search history.

*Primary Examiner* — Susan McCormick Ewoldt
(74) *Attorney, Agent, or Firm* — C. A. Whealy

(57) ABSTRACT

A new and distinct Zonal Geranium plant named 'Pacchogi', characterized by its upright and uniformly rounded plant habit; vigorous growth habit; freely basal branching habit; dark green-colored leaves with broad zonation pattern; freely flowering habit; and cherry red-colored flowers held above the foliar plane on strong peduncles.

1 Drawing Sheet

Botanical designation: *Pelargonium* x *hortorum*.
Cultivar denomination: 'PACCHOGI'.

BACKGROUND OF THE INVENTION

The present invention relates to a new and distinct cultivar of Zonal Geranium plant, botanically known as *Pelargonium* x *hortorum*, and hereinafter referred to by the cultivar name 'Pacchogi'.

The new Zonal Geranium plant is a product of a planned breeding program conducted by the Inventor in Dresden, Germany. The objective of the breeding program is to develop new uniform Zonal Geranium plants with dark green-colored leaves and numerous attractive flowers.

The new Zonal Geranium plant originated from a cross-pollination made by the Inventor in Dresden, Germany during the summer of 2011 of two unnamed proprietary selections of *Pelargonium* x *hortorum*, not patented. The new Zonal Geranium plant was discovered and selected by the Inventor as a flowering plant from within the progeny of the stated cross-pollination in a controlled greenhouse environment in Dresden, Germany during the spring of 2012.

Asexual reproduction of the new Zonal Geranium plant by vegetative terminal cuttings in a controlled greenhouse environment in Dresden, Germany since January, 2013 has shown that the unique features of this new Zonal Geranium plant are stable and reproduced true to type in successive generations.

SUMMARY OF THE INVENTION

Plants of the new Zonal Geranium have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Pacchogi'. These characteristics in combination distinguish 'Pacchogi' as a new and distinct Zonal Geranium plant:

1. Upright and uniformly rounded plant habit.
2. Vigorous growth habit.
3. Freely basal branching habit.
4. Dark green-colored leaves with broad zonation pattern.
5. Freely flowering habit.
6. Cherry red-colored flowers held above the foliar plane on strong peduncles.

Plants of the new Zonal Geranium differ primarily from plants of the parent selections in plant habit as plants of the new Zonal Geranium are more uniform than plants of the parent selections.

Plants of the new Zonal Geranium can be compared to plants of the *Pelargonium* x *hortorum* 'Pacludo', disclosed in U.S. Plant Pat. No. 24,237. In side-by-side comparisons, plants of the new Zonal Geranium differ from plants of 'Pacludo' in the following characteristics:

1. Plants of the new Zonal Geranium are more vigorous than plants of 'Pacludo'.
2. Plants of the new Zonal Geranium are more freely branching than plants of 'Pacludo'.
3. Leaves of plants of the new Zonal Geranium have a broader zonation pattern than leaves of plants of 'Pacludo'.
4. Plants of the new Zonal Geranium are more freely flowering than plants of 'Pacludo'.
5. Plants of the new Zonal Geranium have smaller umbels and flowers than plants of 'Pacludo'.

BRIEF DESCRIPTION OF THE PHOTOGRAPH

The accompanying colored photograph illustrates the overall appearance of the new Zonal Geranium plant showing the colors as true as it is reasonably possible to obtain in colored reproductions of this type. Colors in the photograph may differ slightly from the color values cited in the detailed botanical description which accurately describe the colors of the new Zonal Geranium plant.

The photograph comprises a side perspective view of a typical flowering plant of 'Pacchogi' grown in a container.

DETAILED BOTANICAL DESCRIPTION

The aforementioned photograph and following observations, measurements and values describe plants grown in 19-cm containers during the winter, spring and summer in a glass-covered greenhouse in Dresden, Germany and under cultural practices typical of commercial Zonal Geranium production. During the production of the plants, day temperatures averaged 18° C., night temperatures averaged 16° C. and light levels ranged from 15 kilolux to 100 kilolux. Plants were three months old when the photograph was taken and nine months old when the detailed description was taken. In the detailed description, color references are made to The Royal Horticultural Society Colour Chart, 1995 Edition, except where general terms of ordinary dictionary significance are used.

Botanical classification: *Pelargonium* x *hortorum* 'Pacchogi'.

Parentage:

*Female, or seed, parent*.—Unnamed proprietary selection of *Pelargonium hortorum*, not patented.

*Male or pollen parent*.—Unnamed proprietary selection of *Pelargonium* x *hortorum*, not patented.

Propagation:

*Type*.—By vegetative terminal cuttings.

*Time to initiate roots, summer*.—About 18 days at temperatures about 20° C.

*Time to initiate roots, winter*.—About 22 days at temperatures about 20° C.

*Time to produce a rooted young plant, summer*.—About four weeks at temperatures about 20° C.

*Time to produce a rooted young plant, winter*.—About four weeks at temperatures about 18° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Upright and uniformly rounded plant habit; inverted triangle; densely foliated; vigorous growth habit; rapid growth rate; freely basal branching habit with about 24 lateral branches developing per plant; pinching is not required.

*Plant height, to top of umbels*.—About 35 cm.

*Plant height, to top of foliar plane*.—About 25 cm.

*Plant width*.—About 40 cm.

*Lateral branches*.—Length: About 30 cm. Diameter: About 1 cm. Internode length: About 1 cm to 4 cm. Texture: Pubescent. Color: Close to 146C.

Leaf description:

*Arrangement*.—Typically opposite; simple.

*Length*.—About 5.5 cm.

*Width*.—About 9 cm.

*Shape*.—Rounded; roughly reniform.

*Apex*.—Rounded.

*Base*.—Cordate, open.

*Margin*.—Bi-crenate.

*Venation pattern*.—Palmate.

*Texture, upper and lower surfaces*.—Sparsely pubescent; velvety.

*Color*.—Developing and fully expanded leaves, upper surface: Close to 137A; venation, close to 137A. Developing and fully expanded leaves, lower surface: Close to 138A; venation, close to 143C. Zonation pattern: Intensity: High. Width: Broad, almost covering the entire leaf, about 5 cm. Distance from margin: Close to 5 mm. Color: Close to 200A.

*Petioles*.—Length: About 6 cm. Diameter: About 2 mm. Texture, upper and lower surfaces: Pubescent; rough. Color, upper and lower surfaces: Close to 138B.

Flower description:

*Flower arrangement and flowering habit*.—Single flowers arranged in roughly hemispherical umbels arising from apical leaf axils; umbels displayed above the foliar plane on strong peduncles; flowers face upright to outwardly; freely flowering habit with about 36 flower buds and flowers per umbel and about 60 umbels developing per plant.

*Fragrance*.—None detected.

*Flowering season*.—Plants begin flowering about 90 days after planting; in the garden in Germany, flowering begins in April and continues until frost in the autumn.

*Flower longevity*.—Flowers last about six to ten days on the plant; umbels last about three to four weeks on the plant; flowers persistent.

*Umbel height*.—About 5 cm.

*Umbel diameter*.—About 8 cm.

*Flower diameter*.—About 4 cm.

*Flower depth* (*height*).—About 1.5 cm.

*Flower buds*.—Length: About 1 cm. Diameter: About 5 mm. Shape: Elliptic. Color: Close to 144A.

*Petals*.—Quantity per flower: About six; petals imbricate. Length: About 2 cm. Width: About 2.2 cm. Shape: Spatulate. Apex: Rounded. Base: Cuneate. Margin: Entire. Texture, upper and lower surfaces: Smooth, glabrous; velvety. Color: When opening and fully opened, upper surface: More red than 52A; venation, more red than 52A; color becoming close to 57B with subsequent development. When opening and fully opened, lower surface: Close to 52D; venation, close to 52D; color does not change with development.

*Petaloids*.—None observed on plants of the new *Pelargonium* to date.

*Sepals*.—Quantity per flower: Five arranged in a single whorl. Length: About 1 cm. Width: About 2 mm to 3 mm. Shape: Lanceolate. Apex: Acute. Margin: Entire. Texture, upper surface: Smooth, glabrous. Texture, lower surface: Pubescent. Color, upper and lower surfaces: Close to 144A.

*Peduncles* (*umbel stems*).—Length: About 17 cm. Diameter: About 5 mm. Strength: Strong. Angle: Mostly upright. Texture: Pubescent. Color: Close to 144A.

*Pedicels* (*individual flower stems*).—Length: About 2.5 cm. Diameter: About 2 mm. Strength: Moderately strong; flexible. Texture: Sparsely pubescent. Color: Close to 144B.

*Reproductive organs*.—Androecium: Stamen quantity per flower: About ten. Anther length: About 1 mm to 2 mm. Anther shape: Tubular. Anther color: Close to 199A. Pollen amount: None to scarce. Pollen color: Golden brown. Gynoecium: Pistil quantity per flower: One. Pistil length: About 8 mm. Stigma shape: Five-parted. Stigma color: Close to 50A. Style length: About 2 mm to 3 mm. Style color: Close to 37A. Ovary color: Close to 193A. Seeds and fruits: Seed and fruit development have not been observed on plants of the new Zonal Geranium.

Disease & pest resistance: Plants of the new Zonal Geranium have not been observed to be resistant to pathogens and pests common to Zonal Geraniums.

Temperature tolerance: Plants of the new Zonal Geranium have been observed to tolerate temperatures ranging from about 1° C. to about 35° C. to 40° C.

It is claimed:

1. A new and distinct Zonal Geranium plant named 'Pacchogi' as illustrated and described.

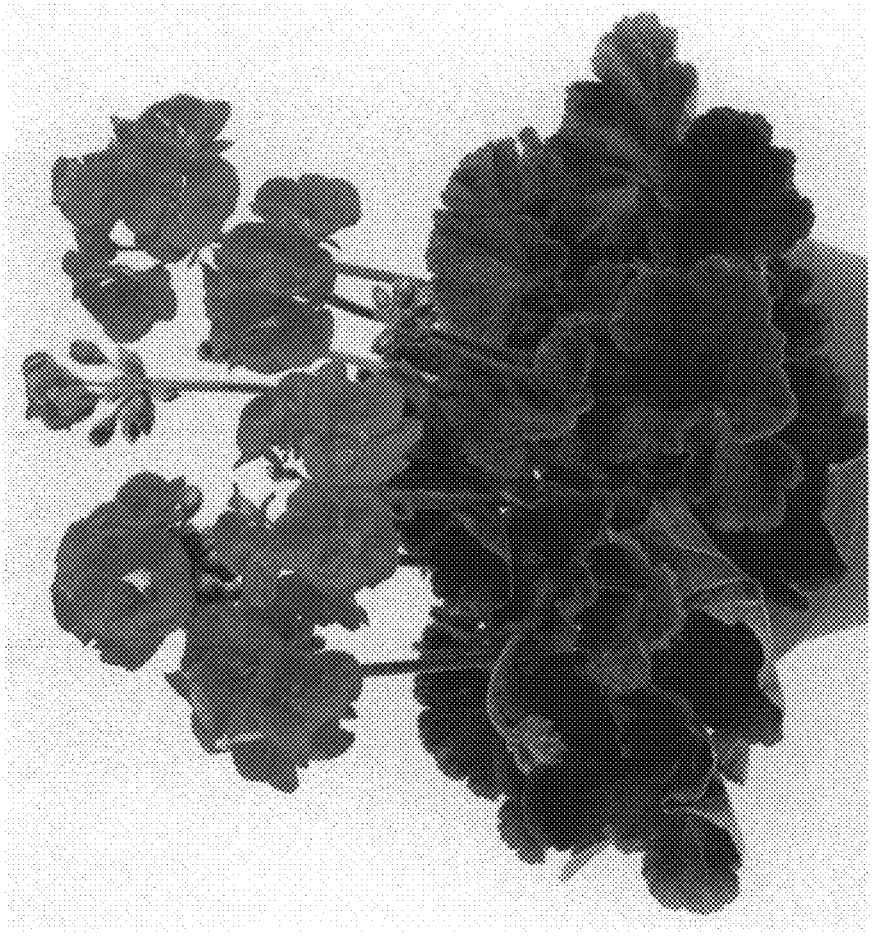

* * * * *